US006932801B1

(12) United States Patent
Samuelsson

(10) Patent No.: US 6,932,801 B1
(45) Date of Patent: Aug. 23, 2005

(54) SANITARY NAPKIN WHOSE REAR PORTION INCLUDES A LONGITUDINALLY EXTENDING RIDGE

(75) Inventor: Ann Samuelsson, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 375 days.

(21) Appl. No.: 10/070,471

(22) PCT Filed: Sep. 6, 2000

(86) PCT No.: PCT/SE00/01720

§ 371 (c)(1),
(2), (4) Date: Mar. 7, 2002

(87) PCT Pub. No.: WO01/17474

PCT Pub. Date: May 15, 2001

(30) Foreign Application Priority Data

Sep. 9, 1999 (SE) .................................... 9903203

(51) Int. Cl.[7] ............................................. A61F 13/15
(52) U.S. Cl. ........................... 604/385.17; 604/385.201
(58) Field of Search ................... 604/385.01, 385.101, 604/385.201, 385.16, 385.17

(56) References Cited

U.S. PATENT DOCUMENTS 4,673,403 A * 6/1987 Lassen et al. .......... 604/385.17
4,804,380 A 2/1989 Lassen et al.
4,846,824 A 7/1989 Lassen et al.
5,672,165 A * 9/1997 Belecky et al. ............. 604/383
5,947,945 A 9/1999 Cree et al.
6,350,257 B1 * 2/2002 Bjorklund et al. ...... 604/385.01
6,447,496 B1 * 9/2002 Mizutani ................ 604/385.17

FOREIGN PATENT DOCUMENTS

EP          0 891 759 A1      1/1999
FR          0 763 839        12/1998
WO          WO 99/25282    *  5/1999   ........... A61F 13/15

* cited by examiner

Primary Examiner—Larry I. Schwartz
Assistant Examiner—C. Lynne Anderson
(74) Attorney, Agent, or Firm—Burns, Doane, Swecker & Mathis, L.L.P.

(57) ABSTRACT

The present invention relates to an absorbent article in the form of a sanitary napkin, a panty liner or an incontinence protector and comprising a front portion, a rear portion, a liquid-permeable top sheet (2), a liquid-impermeable backing sheet (3), and an absorbent body (1) enclosed between the top and backing sheets, wherein the rear portion of the article includes a longitudinally extending ridge-shaped elevation (9) that projects out from that side of the article that contains the top sheet. According to the invention a central string of material (8) extends in the rear portion of the article and the absorbent body (1) between the top sheet (2) and the backing sheet (3) in the rear portion of the article extends around the long sides of said string. The invention also relates to a method of manufacturing such an article.

11 Claims, 3 Drawing Sheets

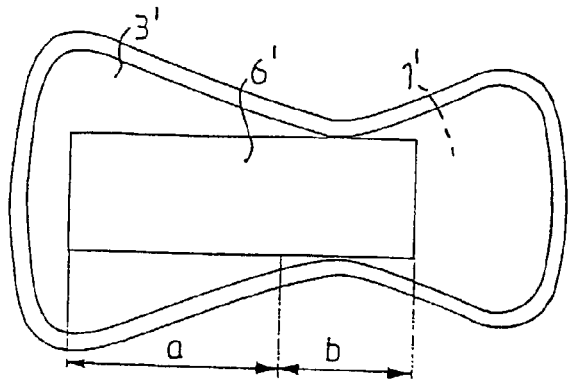
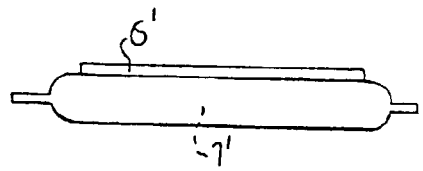
FIG.4A
FIG.4B
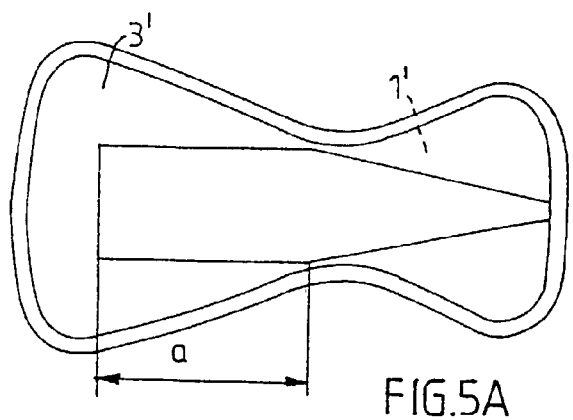
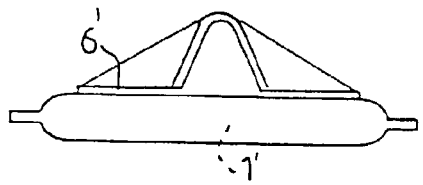
FIG.5A
FIG.5B
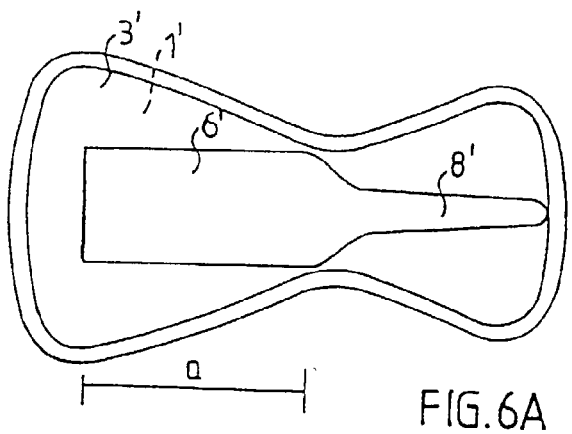
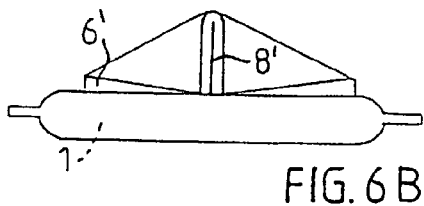
FIG.6A
FIG.6B
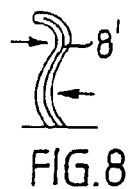
FIG.8

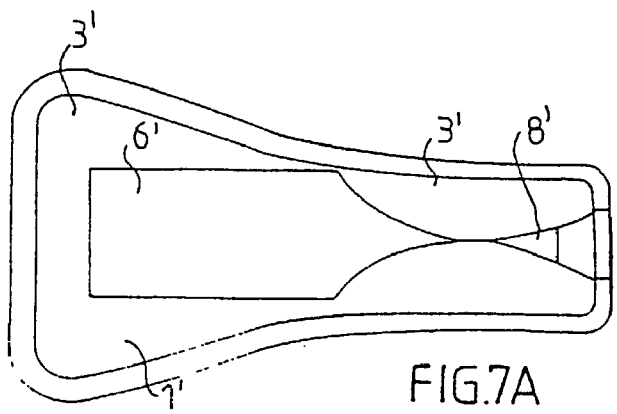
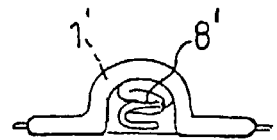
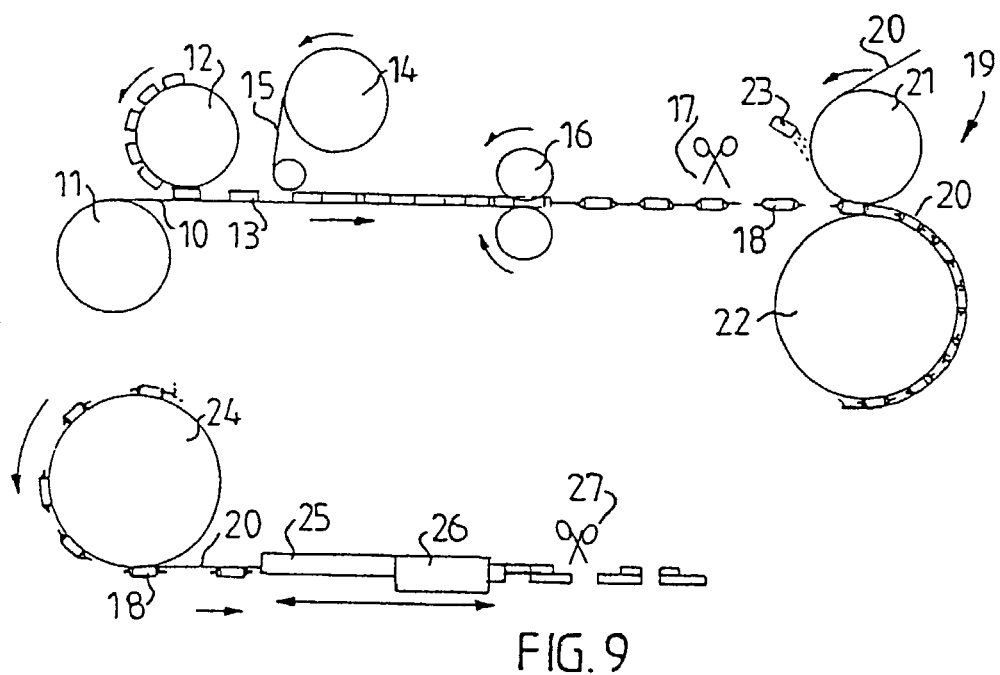
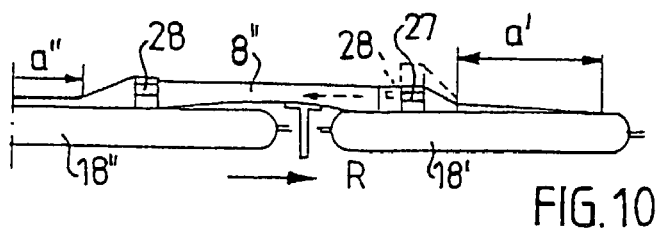

SANITARY NAPKIN WHOSE REAR PORTION INCLUDES A LONGITUDINALLY EXTENDING RIDGE

FIELD OF INVENTION

The present invention relates to an absorbent article in the form of a sanitary napkin, a panty liner or an incontinence protector that has a front and a rear portion and which includes a liquid-permeable top sheet, a liquid-impermeable backing sheet, and an absorbent body enclosed between said top sheet and backing sheet, wherein the rear portion of the article has a longitudinally extending projecting part that projects out in the form of a ridge from that side of the article which includes the top sheet. The invention also relates to a method of manufacturing such an article.

BACKGROUND OF THE INVENTION

Sanitary napkins whose rear portions include ridge-like elevated parts are known to the art, for instance from U.S. Pat. No. 4,673,403, U.S. Pat. No. 4,804,380 and U.S. Pat. No. 4,846,824. The raised ridge-like parts are well adapted to the female anatomy and therewith reduce the risk of menstruation fluid running along the upper side of the napkin to the edges thereof and therewith soiling the undergarments of the wearer. The ridge-like parts also prevent fluid/liquid running backwards when the wearer lies on her back. When wearing such a napkin, the ridge-like part extends between the buttocks of the wearer, therewith causing the napkin to be held safely in position and preventing the napkin from slipping to one side in use. In the case of the known napkins, the ridge-like raised part is either obtained by bending the absorbent body into a longitudinally extending fold and then fastening together those parts of the backing sheet that abut one another in the fold in one or more places, or by including a profiled insert in the absorbent body. When folding the absorbent body in accordance with the first-mentioned method, the absorbent body is liable to break or be thinned out along the fold, therewith impairing the liquid transport properties of the body. The inclusion of an insert complicates the manufacture of the napkin.

The present invention aims to provide an absorbent article of the aforesaid kind in which the ridge-like part curves gently and has been produced without including an insert in the absorbent body.

SUMMARY OF THE INVENTION

These objects are achieved in accordance with the invention with an absorbent article in the form of a sanitary napkin, a panty liner or an incontinence protector which includes a front portion, a rear portion, a liquid-permeable top sheet, a liquid-impermeable backing sheet, and an absorbent body or pad enclosed between the top sheet and backing sheet, and article having in it rear portion a longitudinally outstanding part which extends in the form of a ridge from that side of the article that includes the top sheet, said article being characterised in that a central string of material extends in the rear portion of the article, and in that the absorbent body enclosed between the top and backing sheets extends around the long sides of said string in the rear portion of the article. Folding of the absorbent body around a string of material results in a gently rounded ridge-like elevation.

In one preferred embodiment of the invention, the string comprises a rear portion of a longitudinally extending strip of flexible material that presents a high coefficient of friction to textile material and which extends in the front and the rear portions of the article and is attached to the backing sheet on that side thereof distal from the absorbent body. This ensures that the front portion of the article will not move relative to the undergarments of the wearer then the article is in use.

Those parts of the article which extend around the long sides of the string of tape material extending in the rear portion of the article abut with and are attached to each other in an least one place. The strip of flexible material is preferably comprised of an elastic foam material which is mounted in a stretched state in the rear portion of the article and in a relaxed state in the front portion of said article, wherewith mutually adjacent parts of the string of strip material are fastened together in at least one place. The strip extends symmetrically on both sides of the longitudinal symmetry axis of the article and has in the front portion of said article a width which is greater than half the smallest width of the article in its front portion.

The present invention also relates to a method of manufacturing an absorbent article which comprises a front portion and a rear portion that includes a longitudinally extending elevated portion, said method comprising the steps of:

(a) placing a body of absorbent material on a first sheet of liquid-permeable material;

(b) placing a second sheet comprised of liquid-impermeable material on the body of absorbent material and joining the first and the second sheets together at those parts thereof that lie outside the body of absorbent material, therewith forming a generally flat composite body, characterised by the further steps of (c) placing a strip of flexible material on the second sheet of said composite body and causing said strip to extend over at least a part of a front and a rear portion of the composite body;

(d) fastening the strip to said second sheet in the front portion of the composite body;

(e) forming a longitudinally extending string from that part of the strip which extends in the rear portion of the composite body; and (f) folding those parts of the composite body lying on respective sides of the longitudinal string inwardly around said string and fastening said body parts together in at least one place.

In a preferred embodiment of the invention, said strip is comprised of elastic material and the part of the strip that extends in the rear portion of the composite body is stretched prior to carrying out step (f). The longitudinally extending string is formed by folding or rolling the strip together and fastening those parts of the composite body folded in on respective sides of the longitudinal string of strip material to said string in at least two sections which are mutually spaced apart in the longitudinal direction and which extend around the circumference of the string. In one variant, the part of the strip that extends in the rear portion of the composite body is formed into a longitudinally extending string before the strip is placed on the composite body.

BRIEF DESCRIPTION OF THE DRAWINGS

The invention will now be described with reference to the accompanying drawings, in which

FIGS. 4A, B-7A, B illustrate schematically different steps in the manufacture of an inventive sanitary napkin;

FIG. 8 illustrates schematically a method of folding a rear portion of a friction-enhancing layer fastened to the napkin of FIGS. 4–7;

FIG. 9 is a schematic illustration of a production line for the manufacture of an inventive sanitary napkin;

FIG. 10 illustrates schematically part of the arrangement shown in FIG. 9; and

DESCRIPTION OF EMBODIMENTS

Figure 1:
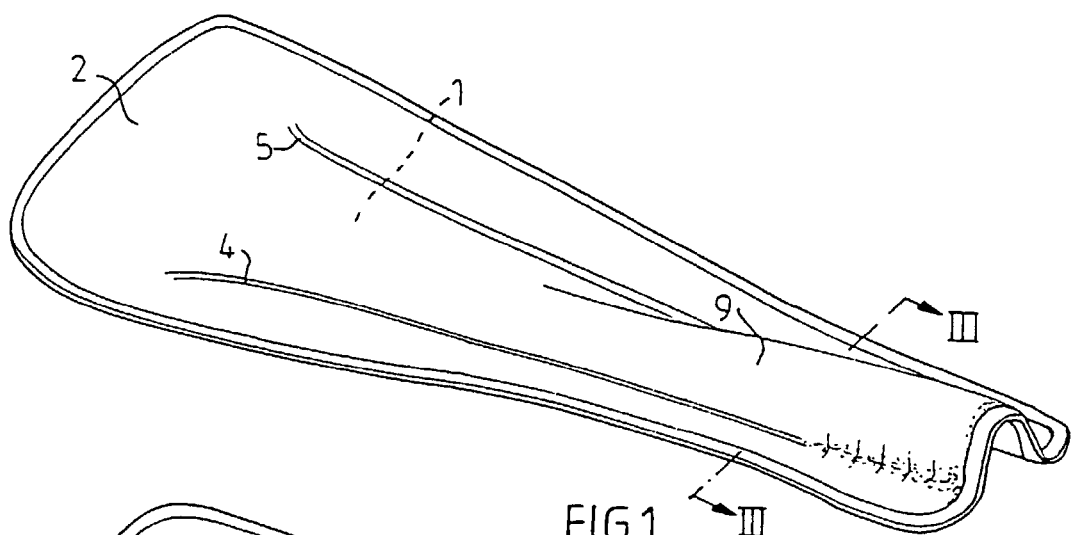
FIG. 1 is a schematic perspective plan view of a sanitary napkin according to one embodiment of the invention.
Figure 2:
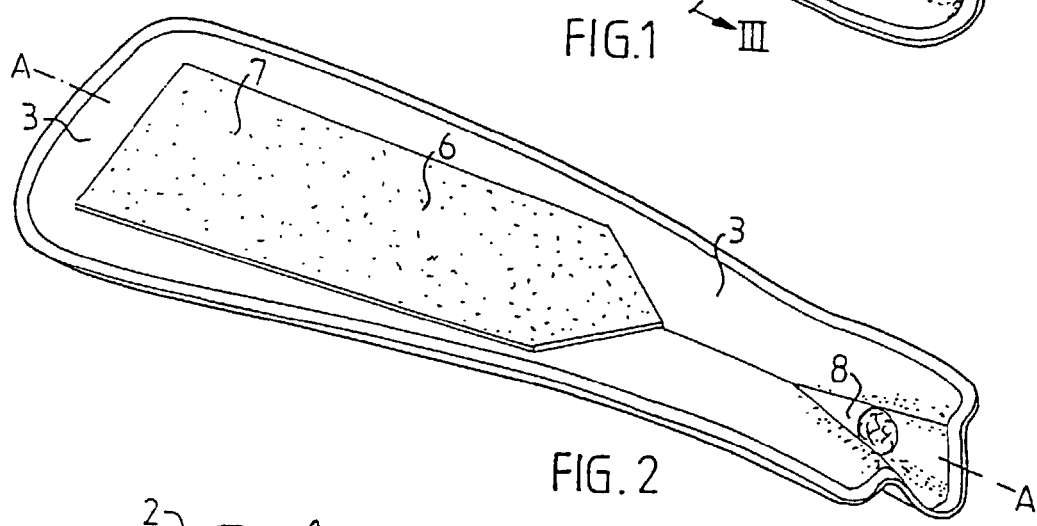
FIG. 2 is a schematic perspective illustration of the sanitary napkin in FIG. 1 taken from beneath.
Figure 3:
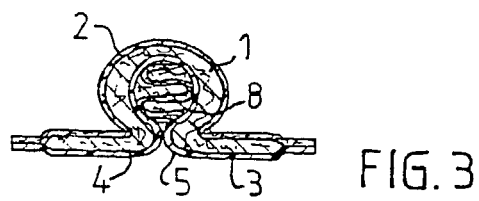
FIG. 3 is a cross-sectional view taken on the line III—III in FIG. 1.

FIGS. 1–3 illustrate a sanitary napkin according to a preferred embodiment of the invention. The napkin includes conventionally an absorbent body or pad 1 enclosed between two casing sheets, i.e. a top sheet 2 and a backing sheet 3. The top sheet and the backing sheet are joined together, e.g. glued or heat-welded, in those sheet parts that externally surround the absorbent body. The napkin also includes on respective sides of its longitudinal symmetry line two compression lines 4, 5 that extend along a major part of the length of the napkin and equidistantly from respective long edges thereof.

The top sheet 2 is comprised of a liquid-permeable material, preferably nonwoven material although other materials may be used, such as perforated plastic film, for instance a thermoplastic material such as polyethylene. The nonwoven sheet may consist of natural fibres, such as cellulose or cotton fibres, or may consist of synthetic fibres, such as polyethylene, polypropylene, polyester, polyurethane, nylon or regenerated cellulose fibres. Alternatively, the top sheet may comprise a lamination. The material in the top sheet is preferably hydrophobic or has been treated so as to obtain a hydrophobic surface. It will be understood that the invention is not restricted to the use of said materials and that all materials that are used as top sheet material in absorbent articles may be used in the top sheet 2.

The backing sheet 3 is comprised of a liquid-impermeable material, preferably plastic film produced from polyethylene, polypropylene or polyester. The backing sheet may also conveniently be microporous, i.e. will allow air and vapour to pass through but not liquid. The backing sheet may alternatively consist of a liquid-permeable material that has been coated with plastic, resin or some other liquid-impervious material. The backing sheet may be given a textile-like feeling, by forming said sheet from a lamination of nonwoven and liquid-impervious material, said nonwoven sheet being faced outwards. All materials used in the backing sheets of absorbent articles can be used in the present context.

The absorbent body 1 is preferably comprised of cellulose fluff, although other materials used for absorbent bodies in absorbent articles can be used in an absorbent body according to the invention. The absorbent body may comprise one or more layers of absorbent material, wherewith so-called superabsorbent material can be mixed in one or more of the layers, and it is also conceivable to form the whole of the lowermost layer in a multilayer absorbent body from super-absorbent material, i.e. the layer that lies proximal to the backing sheet. The absorbent body 1 of the illustrated embodiment comprises a single sheet of cellulose pulp that has been compressed to a density of 0.1–0.2 g/cm$^3$. The cellulose pulp may exist in the form of rolls, bales or sheets that are dry-defibred and converted in a fluffed state to a pulp mat, sometimes while mixing-in so-called superabsorbents, i.e. polymers that are able to absorb liquid in an amount corresponding to several times their own weight. Other materials that can be used are different types of natural fibres, such as cotton fibres, peat fibres or the like. Synthetic absorbent fibres may also be included in the absorbent body.

According to the invention, a strip 6 of flexible material that has a high coefficient of friction with respect to textile material is fastened to the underside of the napkin, e.g. glued thereto. That part of the strip extending in the front portion 7 of the napkin is open to its full width, whereas the rear portion of the strip 6 is folded or rolled together to form a string 8 that extends along the longitudinal symmetry line A—A of the napkin. The rear portion of the napkin is folded around the string 8 and fastened thereto, e.g. glued. This results in a ridge-like elevation 9 on the upper side of the napkin, i.e. the side that is intended to lie in contact with the wearer's body. In the illustrated embodiment, the rear portion of the napkin is folded around the full periphery of the string 8 along a string section and the folded parts of the napkin are fastened together along this section, i.e. by gluing or welding, as will be seen from FIGS. 2 and 3.

When donning the illustrated napkin, the napkin is positioned so that the ridge-like elevation 9 will partially extend between the wearer's buttocks. This provides good protection against rearward leakage. The ridge-like elevation 9 conforms effectively to the female anatomy in other respects and therewith contributes in greatly reducing the risk of liquid running along the upper surface of the napkin and out to the edges thereof. The ridge-like elevation 9 also prevents the napkin from moving sideways as the wearer moves. When the napkin is worn, the front portion 7 of the strip 6 lies against the wearer's undergarments and prevents the front portion of the napkin moving relative to said garments as a result of frictional forces. A sanitary napkin constructed in this manner does not therefore require the provision of an adhesive layer on the backing sheet in order to fasten the napkin to the undergarments of the wearer, since the napkin is held securely in place by the ridge 9 and the friction strip 6.

Because the ridge-like elevation is formed by folding the absorbent body 1 and its casing sheets 2, 3 around the string 8, the ridge 9 obtains a gently curved cross-sectional shape. The width of the ridge can be varied in many ways, for instance by varying the width of the rear portion of the strip 6 or by varying that part of the periphery of the string 8 that is embraced by the absorbent body 1. As will be seen from FIGS. 1 and 2, the ridge 9 is broader in those sections in which the backing sheet 3 is not fastened to the string 8 around the whole of its circumference.

In the illustrated embodiment, the strip 6 is produced from an elastic plastic foam material, preferably foamed polyethylene that has open cells, although other foam materials may be used, such as viscous foam, polyacrylate foam, polyester foam or polystyrene foam having open cell structures. It is preferred to stretch the string 8 before the rear portion of the napkin is folded around the string, and to keep the string stretched as the portion of the napkin folded around said string is fastened thereto. The elastic string tends to return to its pre-stretched state and will therefore contract when the load on the finished napkin is removed. The ridge 9 will therewith obtain a somewhat curved shape in its longitudinal direction, this curvature depending on the extent to which the string 8 is stretched prior to attaching the rear portion of the napkin thereto. The cross-sectional area of the string will decrease somewhat as the string 8 is stretched.

One embodiment of a method of manufacturing a sanitary napkin in accordance with the invention will now be described with reference to FIGS. 4–8.

The sanitary napkin is preferably manufactured continuously, by placing a row or line of absorbent bodies on a travelling first web of material. A second web of material is then placed on top of the absorbent bodies so as to form a composite web consisting of two casing sheets and intermediate absorbent bodies. Individual napkins, which are still not provided with friction strips, are then cut from the composite web.

FIGS. 4A, B-7A, B illustrate the various steps in the final stages of the method of providing a sanitary napkin with a ridge-like elevation, as seen in plan view with the backing sheet facing towards the viewer and in side view seen from the rear short side of the napkin respectively. Those components of the napkin shown in FIGS. 4A, B-7A, B that find correspondence in components shown in FIGS. 1–3 have been identified with the same reference signs to which a prime has been added.

In a first step (FIGS. 4A; B), a strip 6 of foam material is placed on the backing layer 3' of the napkin cut from said composite web and the strip 6' is fastened to the backing sheet 3' in the front portion of the napkin, within the distance reference a in FIG. 4A. The strip is preferably glued to said sheet, although it may also be welded thereto, e.g. spot-welded. The strip is not fastened to the backing sheet in the rear portion of the napkin within the distance identified by reference b in FIG. 4A.

In the second step of the final stage (FIGS. 5A, B, 6A, B) the strip 6' is stretched in the rear portion of the napkin and its side-edges folded in towards each other.

The resultant string 8' is then folded into an inverse S-shape, as shown schematically in FIG. 8 and is compressed so that the folded parts of said string 8' will lie in abutment with one another.

Finally (FIGS. 7A, B), the absorbent body 1' in the rear portion of the napkin is folded around the string 8' and fastened thereto. The absorbent body is folded around the full circumference of the string 8' within one section thereof, and those parts of the backing sheet 3' which are therewith brought into mutual abutment are fastened together in this string section. The string will therewith be fully embraced by the absorbent body within said string section, thereby preventing the string 8' of elastic material from changing its shape in said string section as a result of its inherent spring forces.

As will be understood, it is not necessary for the rear portion of the napkin to include a section in which the string 8' is fully embraced by the absorbent body and that the string 8' can be prevented from departing from its compressed state, by virtue of its intrinsic spring force, and from taking a more extended state, by fastening the compressed parts of the string 8' together locally, e.g. at the beginning of the string and at its free end or in an intermediate portion of said ends. However, it is preferred to sustain the string in a compressed state with the aid of absorbent body sections folded around said string, since this obviates the need of applying glue to the string and therewith significantly facilitates manufacture of the napkin.

FIG. 9 is a schematic illustration of an inventive napkin production line.

A web 10 of top sheet material, e.g. nonwoven material, is unwound from a storage reel 11 and transported on a transporter (not shown), e.g. a vacuum transporter, to the right in FIG. 10, as indicated with an arrow. A device 12 for laying a row of line of absorbent bodies 13 on the web 10 is positioned downstream of the reel 11. Downstream of the device 12 is a second storage reel 14 from which a second web 15 comprising backing material is unwound and placed on the line of absorbent bodies 13. The composite web consisting of the two webs 10, 15 and the absorbent bodies 13 is then passed through a device 16 located downstream of the device 14 and functioning to fasten the webs 10, 15 together at parts which lie externally of the bodies 13. The webs 10, 15 are preferably glued together, wherewith the glue is conveniently applied to the web 15 immediately said web is placed over the absorbent bodies 13. The webs may alternatively be welded together, e.g. by ultrasound welding. The composite web then passes through a cutting or punching device 17 in which individual absorbent articles 18 are cut or punched from the composite web. The components described hitherto are typical in production lines for sanitary napkins and like articles, as are also other components, for instance such as further devices for laying bodies on top of the absorbent bodies 13 to form multilayer absorbent bodies, or means for providing the napkin with compression lines or elastic elements, all of which may be included in the production line.

Located downstream of the punch 17 is a device 19 for applying and fastening a strip of plastic foam material 20 to the backing sheet 15 of each article 18 cut from the composite web. The articles 18 and a strip-forming web of material 20 taken from a storage reel (not shown) are passed through the nip of a pair of rolls 21, 22 in the device 19. Prior to entering the roll nip, the web 20 is provided intermittently with a glue layer on parts of the side facing towards the article 18, with the aid of an intermittently operating glue applicator 23. The web 20 and the articles 18 fastened thereon are then passed to a transfer wheel 24 which has a higher peripheral speed than the roll 22. Those parts of the web 22 on which no articles 18 are fastened will thereby be stretched and the spacing between the articles 18 therewith increased. Located downstream of the transfer wheel 24 is a device 25 in which those sections of the web in which no articles 18 are fastened are folded together in the manner shown in FIGS. 4A–6B and FIG. 8, so as to form a string. The web 20 and appendant articles 18 then pass through a device 26 in which parts of the articles 18 are folded-in around the formed string and fastened thereto in the manner shown in FIGS. 7A, B. After exiting from the device 26, the web 20 and the articles 18 fastened thereto pass through a cutting or punching device 26 in which individual napkins provided with ridge-like elevations are cut-out.

In the described arrangement, the articles 18 are fully symmetrical in shape, such that the front and rear portions of the articles are of similar shape, and glue is applied in the device 19 so that mutually facing ends of the articles 18 will be either rear portions or front portions of the napkin. As illustrated schematically in FIG. 10, the device 25 may include two sets of hinged folding plates 27, 28 that can be folded to a compressed S-shape and can be moved relative to each other in the direction of web movement and also relative to the conveyor (not shown) on which the web 20 and its appendant articles are transported. The devices 25, 26 can move reciprocatingly relative to the line of articles, which are moved with the aid of a conveyor (not shown). In a first position, the folding plates 27, 28 are placed adjacent each other and immediately upstream of the section α' of the strip-like web 20 fastened to the backing sheet of the front portion of an article 18'. The folding plates are then moved in the direction of movement R of the articles 18', 18''' at the same speed as said articles, and the web 20 is folded into an S-shape locally, by folding together the plates 27, 28. When folding of the plates is finished, the plate 28 is moved in the upstream direction relative to the plate 27 and gives the web 20 an S-shape during its upstream movement. The plate 28 is moved in the upstream direction to a point slightly spaced from that part a" of the section of web 20 fastened to the article 18". The articles 18', 18" will now be situated in the device 26, and the mutually opposing rear portions of the articles 18', 18" are folded around the formed string 8" and fastened thereto. As the rear portions of the articles 18', 18" are folded-in, the devices 25, 26 move in the movement direction R at the same speed as the web 20 and the articles 18', 18". The devices 25, 26 are then moved back in the upstream direction, so as to be positioned correctly for forming strings in subsequent pairs of articles 18 in the process line.

Figure 11:
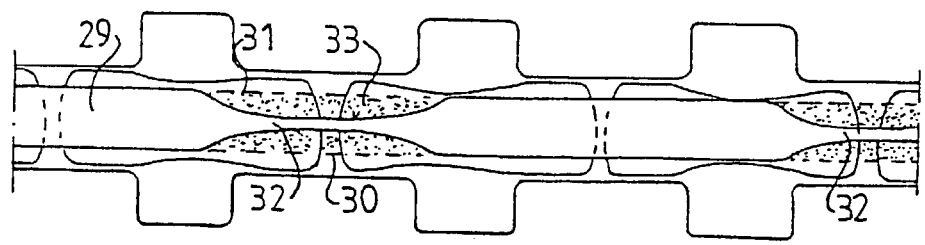
FIG. 11 illustrates schematically a further method of manufacturing an inventive sanitary napkin.

One variant of the described embodiment of a method of manufacturing sanitary napkins in accordance with the invention is shown schematically in FIG. 11. This variant differs from the earlier described method by virtue of applying the strip-like web 29 to the web 30 of napkin blanks 31 in a ready-folded shape, said blanks each comprising an absorbent body enclosed between a top sheet and a backing sheet. The strings 32 of strip-like material have thus already been produced when the web 29 of strip-like material is placed on the web 30. In the variant shown in FIG. 11, the web 30 is comprised of a coherent line of napkin blanks 31. The web 30 of napkin blanks is produced conventionally, e.g. in a process line in accordance with the line described with reference to FIG. 9, although without the short sides of the blanks 31 being cut-out during passage through the cutting or punching device in said process line. The web of backing material faces towards the viewer in FIG. 11.

Prior to applying the web 29 of strip-like material to the web 30 of napkin blanks, the web 30 is provided with a glue string 38 that has a width corresponding to the greatest width of the web 29 and that extends symmetrically on respective sides of the longitudinal symmetry line of the web 30. When glue is applied, the underside of the web 29, including the undersides of the string 32, will adhere to the web 30 of napkin blanks. When the web 29 has fastened to the web 30, the web 30 is folded around its longitudinal symmetry line, meaning that the web 30 located within the regions of the strings 32 will be folded around said strings and fastened thereto and also to themselves. Individual napkins are then cut from the web, by mutually separating the short sides of mutually adjacent napkin blanks. Although not preferred, it is, of course, possible to cut individual napkin blanks from the web 30 prior to applying the web 29 thereto.

The sanitary napkins produced in this way are suitably packed in the aforesaid folded state, since it is easier to obtain a uniform product stack with the napkins in this form than if the napkins were first allowed to adopt their three-dimensional shape with an upstanding curved ridge in their rear portions. Naturally, it is also possible to construct the device 26 in the way described with reference to FIGS. 9 and 10, so that the articles 18, 18' can be fully folded around their longitudinal symmetry axes and packed in a folded-up state.

The napkin blanks illustrated in FIG. 11 include so-called wings which, when the napkin is used, are intended to be folded around the edges of the wearer's panties in order to prevent soiling of the garment. Such wings will, of course, add further security against lateral movement of a sanitary napkin relative to panties.

The aforedescribed embodiments can, of course, be modified within the scope of the invention, particularly with respect to dimensions of the manufactured napkins. When a sanitary napkin intended for night use shall be produced, it may be appropriate to make the rear portion of the napkin wider than when a panty protector shall be produced. When the front and rear portions of the napkins have different shapes, it is necessary to modify the described processes so that each alternate napkin in the napkin line will be turned so that the front and rear portions of the napkin lie adjacent to the front and rear portions of adjacent napkins, or the lengths of the strings of strip material must also be adapted to the length of the rear portions of the napkins, i.e. so that each string will extend solely over the rear end of a single napkin. The manufacturing arrangement may also include further components, for instance when the napkin shall include a liquid dispersion layer between the top sheet and the absorbent body. The invention is therefore restricted solely by the contents of the accompanying claims.

What is claimed is:

1. An absorbent article comprising a front portion, a rear portion, a liquid-permeable top sheet, a liquid-impermeable backing sheet, and an absorbent body enclosed between the top and backing sheets, wherein the rear portion of the article includes a longitudinally extending ridge-shaped elevation that projects out from the side of the article that contains the top sheet, wherein a central string of material extends in the rear portion of the article along the backing sheet on the side thereof distal from the absorbent body, and the top sheet, the backing sheet and the absorbent body enclosed therebetween in the rear portion of the article extend around the long sides of said string, wherein those portions of the article which, in the rear portion of said article, extend around the long sides of the string of strip material abut one another and are fastened to each other in at least one place.

2. An absorbent article comprising a front portion, a rear portion, a liquid-permeable top sheet, a liquid-impermeable backing sheet, and an absorbent body enclosed between the top and backing sheets, wherein the rear portion of the article includes a longitudinally extending ridge-shaped elevation that projects out from the side of the article that contains the top sheet, wherein a central string of material extends in the rear portion of the article; the top sheet, the backing sheet and the absorbent body enclosed therebetween in the rear portion of the article extend around the long sides of said string, and wherein the string comprises a rear portion of a longitudinally extending strip of flexible material that has a high coefficient of friction with respect to textile material and which extends in the front and the rear portion of the article and is fastened to the backing sheet on the side thereof that lies distal from the absorbent body.

3. An absorbent article according to claim 2, wherein the strip of flexible material is an elastic foam material.

4. An absorbent article according to claim 3, wherein the elastic foam material is mounted in the rear portion of the article in a stretched state and in the front portion of the article in a relaxed state.

5. An article according to claim 3, wherein mutually adjacent portions of the material in the string of strip material are fastened to each other in at least one place.

6. An article according to claim 2, wherein the strip extends symmetrically on both sides of the longitudinal symmetry axis of the article and has in the front portion of said article a width which is greater than half the smallest width of the article in its front portion.

7. A method of manufacturing an absorbent article which comprises a front portion and a rear portion and which includes a longitudinally extending elevated section in its rear portion, the method comprises;
  (a) placing a body of absorbent material on a first sheet of liquid-impermeable material;
  (b) placing on the body of absorbent material a second sheet of liquid-impermeable material, and joining together the first and second sheets in those parts of the sheets that extend beyond the body of absorbent material, therewith forming a generally flat composite body;
  (c) placing on the second sheet of the composite body a strip of flexible material that extends over at least a part of a front and a rear portion of the composite body;
  (d) fastening the strip to the second sheet in the front portion of the composite body;
  (e) forming that part of the strip which extends in the rear portion of the composite body into a longitudinally extending string; and
  (f) folding those parts of the composite body that lie on respective sides of the longitudinal string of strip material in around said string and fastening said parts together in at least one place.

8. A method according to claim 7, wherein the strip is comprised of an elastic material, and the part of said strip that extends in the rear portion of the composite body is stretched prior to carrying out step (f).

9. A method according to claim 7, wherein the longitudinally extending strip is shaped by folding or rolling the strip together.

10. A method according to claim 7, wherein by fastening the parts of the composite body that have been folded-in on respective sides of the longitudinal string of strip material to said string in at least two longitudinally spaced sections that extend around the string circumference.

11. A method according to claim 7, wherein forming that part of the strip which extends in the rear portions of the composite body into a longitudinally extending strip prior to placing the strip on the composite body.

* * * * *